United States Patent [19]

Green et al.

[11] Patent Number: 5,718,360

[45] Date of Patent: *Feb. 17, 1998

[54] SURGICAL APPARATUS AND DETACHABLE ANVIL ROD THEREFOR

[75] Inventors: David T. Green, Westport; Jonathan Wilson; Patrick Flanagan, both of Fairfield, all of Conn.

[73] Assignee: United States Surgical Corporation, Norwalk, Conn.

[*] Notice: The portion of the term of this patent subsequent to Sep. 8, 2012, has been disclaimed.

[21] Appl. No.: 341,680

[22] Filed: Nov. 17, 1994

Related U.S. Application Data

[63] Continuation of Ser. No. 941,746, Sep. 8, 1992, Pat. No. 5,368,215.

[51] Int. Cl.[6] .................................................. A61B 17/115
[52] U.S. Cl. ...................................... 227/179.1; 227/19
[58] Field of Search ................................ 227/179.1, 19, 227/180.1, 175.1

[56] References Cited

U.S. PATENT DOCUMENTS

| | | |
|---|---|---|
| 3,160,157 | 12/1964 | Chisman . |
| 3,193,165 | 7/1965 | Akhalaya et al. . |
| 3,388,847 | 6/1968 | Kasulin et al. . |
| 3,593,903 | 7/1971 | Astafiev et al. . |
| 4,198,982 | 4/1980 | Fortner et al. . |
| 4,304,236 | 12/1981 | Conta et al. . |
| 4,319,576 | 3/1982 | Rothfuss . |
| 4,379,457 | 4/1983 | Gravener et al. . |
| 4,473,077 | 9/1984 | Noiles et al. . |
| 4,476,863 | 10/1984 | Kanshin et al. . |
| 4,485,817 | 12/1984 | Swigget . |

(List continued on next page.)

FOREIGN PATENT DOCUMENTS

| | | |
|---|---|---|
| 1136020 | 12/1979 | Canada . |
| 0190022 | 8/1986 | European Pat. Off. . |
| 282157 | 9/1988 | European Pat. Off. . |
| 1461464 | 12/1966 | France . |
| 1588250 | 4/1970 | France . |
| 2443239 | 12/1979 | France . |
| 1057729 | 5/1959 | Germany . |
| 3301713 | 7/1984 | Germany . |
| 7711347 | 4/1979 | Netherlands . |
| 2073086 | 10/1981 | United Kingdom . |
| 87/04915 | 8/1987 | WIPO . |
| 9006085 | 6/1990 | WIPO . |

OTHER PUBLICATIONS

"Use of the Stapler in Interior Reception for Cancer of the Rectosigmoid", Resnick et al., Israel Journal of Medical Sciences, vol. 19, 1983, pp. 128–133.

"New Method of Bowel Stoma Formation", American Journal of Surgery, vol. 152, Nov. 1986, pp. 545–548.

EEA Anvil with a Separate Short-Shaft—Non Confidential Disclosure Agreement, Sep. 17, 1981.

"Minimally Invasive Colon Resection (Laparoscopic Colectomy)", Jacobs et al., Surgical Laparoscopy & Endoscope, vol. 1, No. 3, Sep. 1991, pp. 144–150.

U.S. Surgical Corporation, "Auto Suture Information Booklet" 1990.

*Primary Examiner*—Rinaldi I. Rada
*Assistant Examiner*—Boyer Ashley

[57] ABSTRACT

A detachable anvil rod for use with an apparatus for circular fastening of hollow organs is provided. An elongated rod member has a proximal end portion, a distal end portion and an irregular surface portion intermediate the proximal and distal end portions. The irregular surface portion includes a plurality of grooves which define a plurality of raised ridges. The ridges are adapted to engage grasping surfaces of a grasping tool so as to minimize potential of slippage, thus enhancing the maneuvering procedure of the anvil rod about the operative site. The anvil rod also includes a narrowly configured mounting portion which enables the rod to be applied to and mounted within the distal end of the stapling apparatus from a variety of angular positions. An apparatus which incorporates the improved detachable anvil rod is also described.

19 Claims, 8 Drawing Sheets

U.S. PATENT DOCUMENTS

| | | |
|---|---|---|
| 4,505,272 | 3/1985 | Utyamyshev . |
| 4,573,468 | 3/1986 | Conta et al. . |
| 4,576,167 | 3/1986 | Noiles . |
| 4,592,354 | 6/1986 | Rothfuss . |
| 4,603,693 | 8/1986 | Conta et al. . |
| 4,646,745 | 3/1987 | Noiles . |
| 4,700,703 | 10/1987 | Resnick et al. . |
| 4,703,887 | 11/1987 | Clanton et al. . |
| 4,817,847 | 4/1989 | Redtenbacher et al. . |
| 4,848,367 | 7/1989 | Avant et al. . |
| 4,873,977 | 10/1989 | Avant et al. . |
| 5,042,161 | 8/1991 | Hodge . |
| 5,104,025 | 4/1992 | Main et al. . |
| 5,112,156 | 5/1992 | Granger et al. . |
| 5,119,983 | 6/1992 | Green et al. . |
| 5,156,222 | 10/1992 | Green et al. . |
| 5,368,215 | 11/1994 | Green et al. ............ 227/19 X |

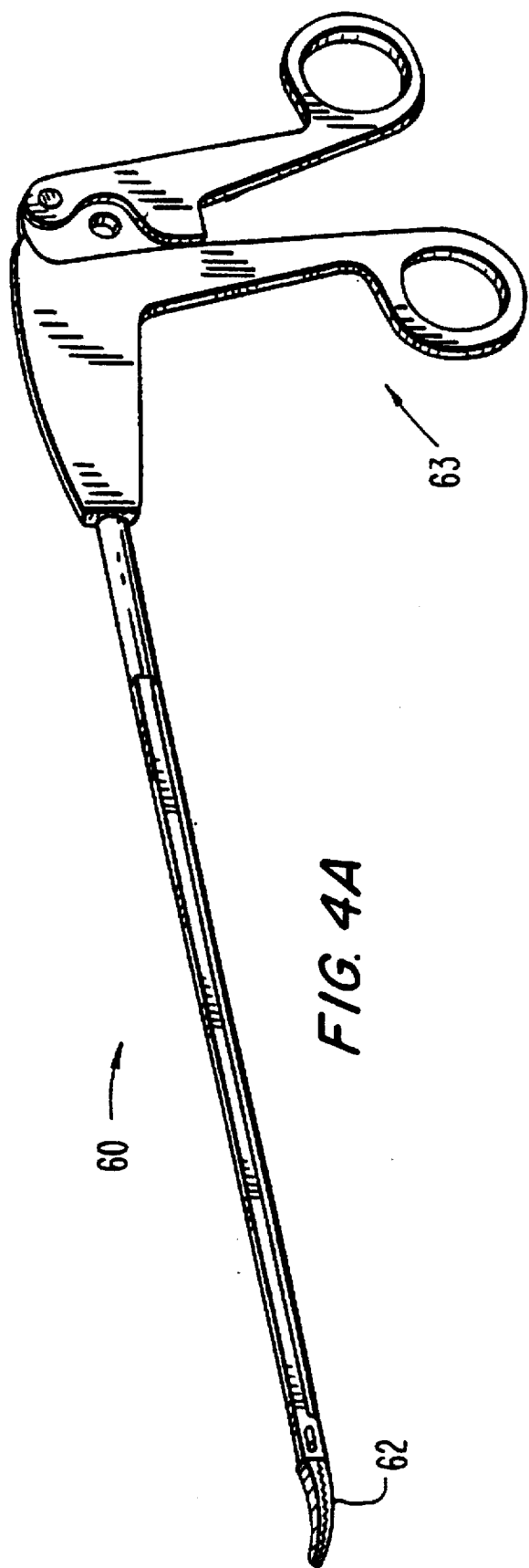
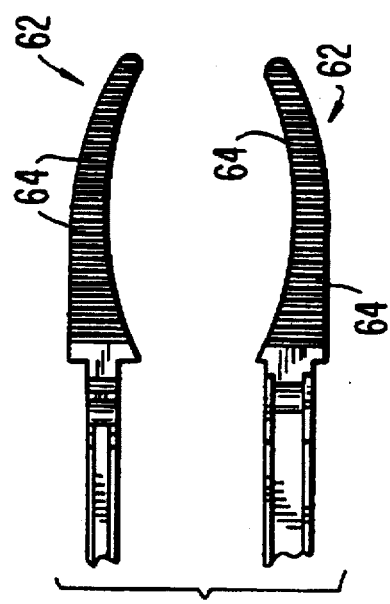
FIG. 4A
FIG. 4B

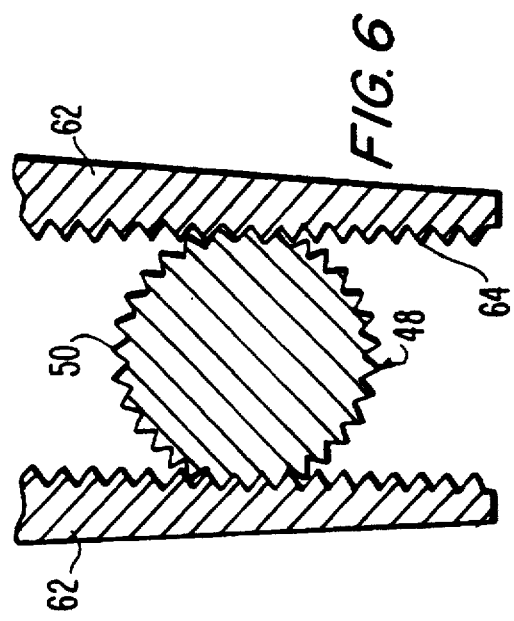
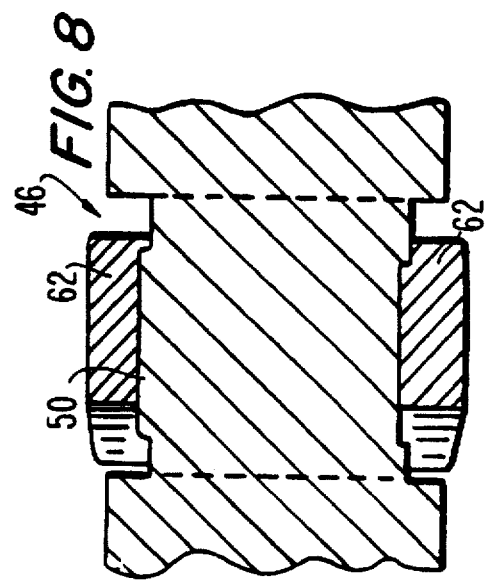
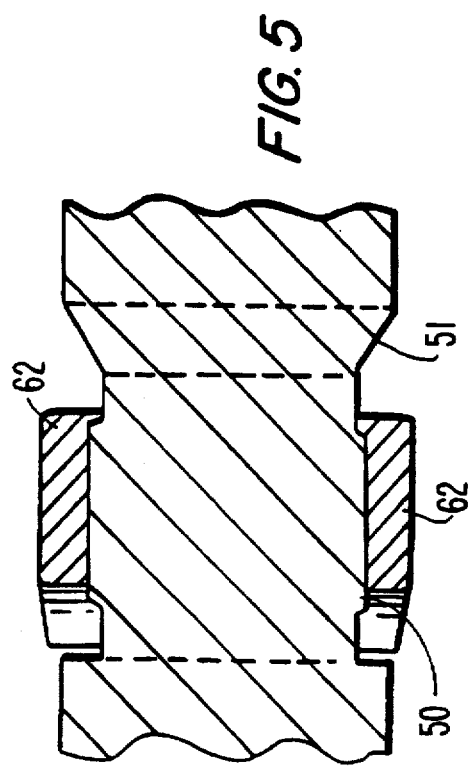
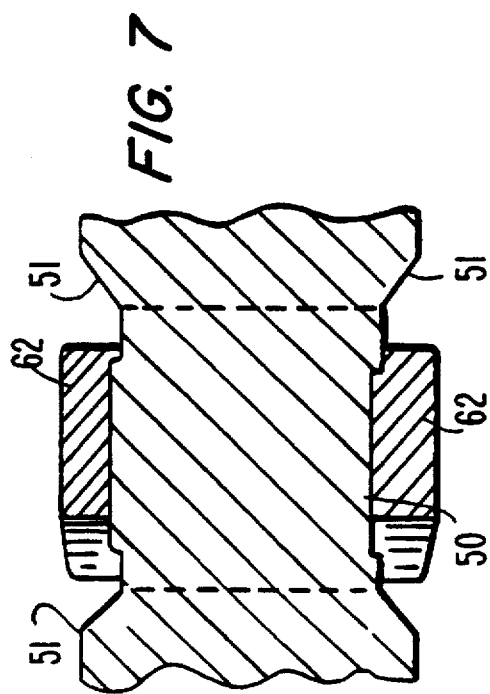

SURGICAL APPARATUS AND DETACHABLE ANVIL ROD THEREFOR

This is a continuation of application Ser. No. 07/941,746 filed Sep. 8, 1992, now U.S. Pat. No. 5,368,215.

BACKGROUND OF THE INVENTION

1. Field of the Invention

The present invention relates generally to an apparatus for performing circular anastomosis of hollow tissue organs having a detachable anvil rod of improved structure. The invention is also directed to a detachable anvil rod having improved structure.

2. Description of the Prior Art

Anastomosis is the surgical joining of separate hollow organ sections so that the sections intercommunicate with each other. Typically, the anastomosis procedure follows surgery in which a diseased or defective section of hollow tissue is removed and the remaining end sections are to be joined. Depending on the desired anastomosis procedure, the end sections may be joined by either circular, end-to-side or side-to-side organ reconstruction methods.

In a circular anastomosis procedure, the two ends of the organ sections are joined by means of a stapling instrument which drives a circular array of staples through the end sections and simultaneously cores any overlapping tissue to free the tubular passage.

Examples of instruments for performing circular anastomosis of hollow organs are described in U.S. Pat. Nos. 4,304,236, 4,379,457, 4,573,468, 4,576,167, 4,603,693, 4,646,745 and 5,119,983. These instruments typically include an elongated shaft having a handle portion at a proximal end to actuate the instrument and a staple holding component disposed at a distal end. An anvil component including an anvil rod with attached anvil head is mounted to the distal end. Opposed end portions of the organs to be stapled are clamped between the anvil head and the staple holding component. The clamped tissue is stapled by driving one or more staples from the staple holding component so that the ends of the staples pass through the tissue and are clinched by the anvil head.

In some applications of the circular anastomosis procedure, the anvil rod with attached anvil head is mounted to the distal end of the shaft prior to insertion of the instrument into the tissue to be anastomised. However, in other applications, it is preferable to utilize a detachable anvil rod which may be mounted to the instrument subsequent to positioning of the instrument and the anvil component within their respective tissue sections. In such instances, the stapling instrument and the anvil component are separately applied to the operative site. Each tissue section is then secured to their respective anvil or staple holding component by a purse string. The anvil component is mounted to the surgical instrument by inserting a mounting portion of the anvil rod within the distal end of the instrument so that a mounting mechanism within the instrument securely engages the rod. Preferably, preparation of the tissue sections to be joined and mounting of the anvil rod to the instrument are performed using minimally invasive surgical techniques, i.e., under laparoscopic guidance.

FIG. 1 illustrates a detachable anvil rod 10 which is presently used with instruments of the type described and in the aforedescribed manner. This anvil rod is a component of the PREMIUM CEEA™ instrument which is manufactured by United States Surgical Corporation and is the subject of U.S. Pat. No. 5,119,983, the contents of which are incorporated herein by reference. The anvil rod includes a mounting portion 12 which has a pointed conical shape at the mounting end, which is inserted within the elongated shaft of the stapling instrument to engage the rod mounting mechanism within the shaft to effect the mounting. The central portion of the anvil rod includes external splines 14 for properly aligning the rod with the staple firing mechanism and an anvil head mounting portion 16 to house the anvil head. The anvil head mounting portion may also include external splines 18 which properly align the anvil head with the stapling firing mechanism to ensure proper reception of the ejected staples into the staple receiving buckets within the anvil head.

Although the detachable anvil rod illustrated in FIG. 1 has many advantages in its application, it would be advantageous to improve the mounting portion. For example, a mounting portion which is relatively narrowly configured may increase user flexibility and facilitate mounting of the rod, particularly when the surgery is performed under laparoscopic guidance, by increasing the range of angular positions at which the rod may be oriented and inserted within the distal end of the apparatus during mounting. Another possible improvement to the rod involves providing structure which will facilitate grasping of the rod with a grasping instrument (e.g., a laparoscopic instrument) so as to enhance maneuvering of the rod about the operative site where blood and other bodily fluids are present.

Accordingly, the present invention is directed to an anvil rod and related applications which has improved structure to facilitate mounting of the rod and maneuvering of the rod about the operative site. The improved structure also facilitates use of the rod during endoscopic or laparoscopic procedures.

SUMMARY OF THE INVENTION

The present invention is directed to a detachable anvil rod for use with an apparatus for performing circular anastomosis. The anvil rod comprises an elongated rod member having a proximal end portion, a distal end portion and an annular irregular surface portion intermediate the proximal and distal end portions. The irregular surface portion is adapted to be engaged by the grasping surfaces of grasping means so as to facilitate gripping engagement therebetween while avoiding slippage when maneuvering the anvil rod about the operative site. In a preferred embodiment, the irregular surface portion comprises a plurality of grooves and ridges and has a reduced cross-section relative to portions of the rod adjacent the irregular surface portion.

The proximal end portion of the anvil rod includes a conical shaped mounting portion which is narrow in configuration to facilitate mounting the rod to the distal end of the apparatus. The mounting portion includes a mounting tip which defines an arcuate surface. In an alternative embodiment, the mounting tip defines a piercing point to facilitate penetration through tissue. The mounting tip defines an angle ranging from about 5° to about 40°. Preferably, the angle defined by the mounting tip is about 20°.

The present invention is also directed to a surgical apparatus for performing circular anastomosis of first and second tissue sections. The apparatus comprises elongated tubular means having a proximal and a distal end, means for firing a plurality of fasteners from the distal end of the elongated tubular means and anvil means detachably mounted to the distal end of the elongated tubular means. The anvil means includes an anvil rod having proximal and distal end portions and an anvil head mounted to the distal end portion of the anvil rod. The anvil rod includes an irregular surface portion intermediate the proximal and distal end portions thereof. The irregular surface portion preferably includes a plurality of grooves which define a plurality of raised ridges. The ridges are adapted to engage the gripping surfaces of a grasping tool so as to minimize the potential of slippage and thus enhance maneuvering of the anvil rod about the operative site. The grooves may extend in a longitudinal direction or may be multi-directionally formed as by knurling.

The anvil rod preferably also includes a plurality of longitudinally extending external splines. The external splines are engagable with cooperating longitudinally extending internal splines formed within the distal end of the elongated tubular means to properly align the anvil rod with the fastener firing means.

The distal portion of the anvil rod preferably includes a plurality of longitudinally extending external splines which are engagable with cooperating longitudinally extending internal splines formed within the anvil head to properly align the anvil head with the anvil rod and the fastener firing means.

BRIEF DESCRIPTION OF THE DRAWINGS

FIG. 4A is a perspective view of a grasping tool suitable for grasping and manipulating the anvil rod of the present invention;

FIG. 4B is a plan view of the gripping surfaces of the grasping tool shown in FIG. 4A;

FIG. 5 is a cross-sectional view taken along lines 5—5 of FIG. 3 illustrating the irregular surface portion of the anvil rod of the present invention;

FIG. 6 is a cross-sectional view taken along lines 6—6 of FIG. 3 illustrating the interlocking engagement of the ridges of the irregular surface portion of the rod by the gripping surfaces of the grasping tool of FIG. 4A;

FIG. 7 is a cross-sectional view similar to the view of FIG. 5 illustrating an alternative embodiment of the anvil rod of the present invention;

FIG. 8 is a cross-sectional view similar to the view of FIG. 5 illustrating another alternative embodiment of the anvil rod of the present invention;

DETAILED DESCRIPTION OF THE PREFERRED EMBODIMENTS

Figure 1:
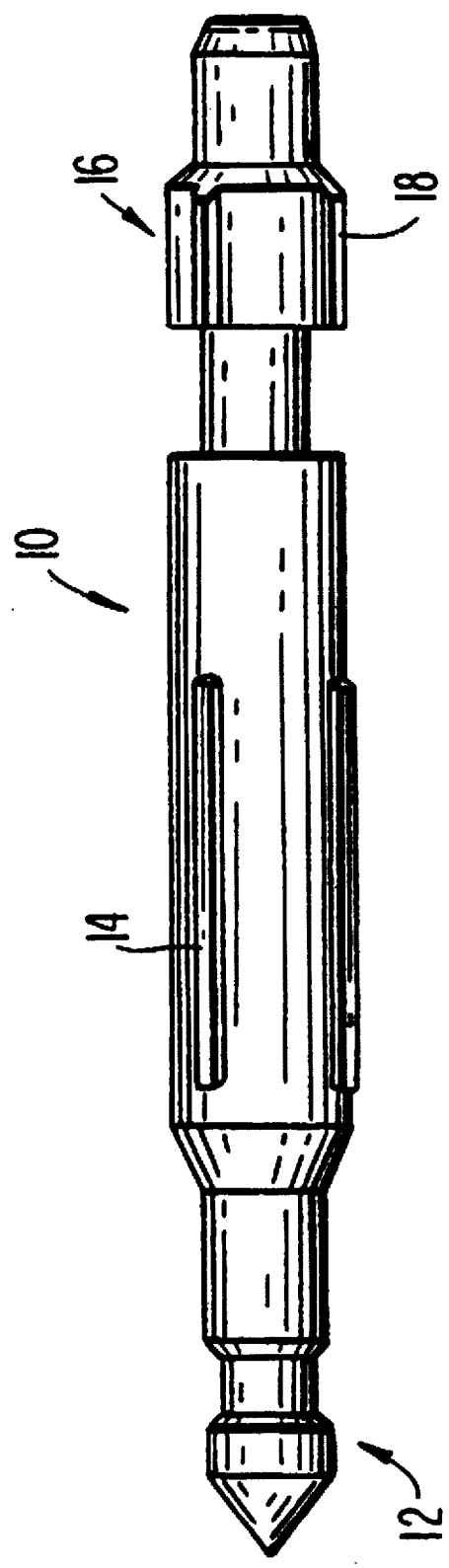
FIG. 1 is a side view of the detachable anvil rod of the type disclosed in U.S. Pat. No. 5,119,983.
Figure 2:
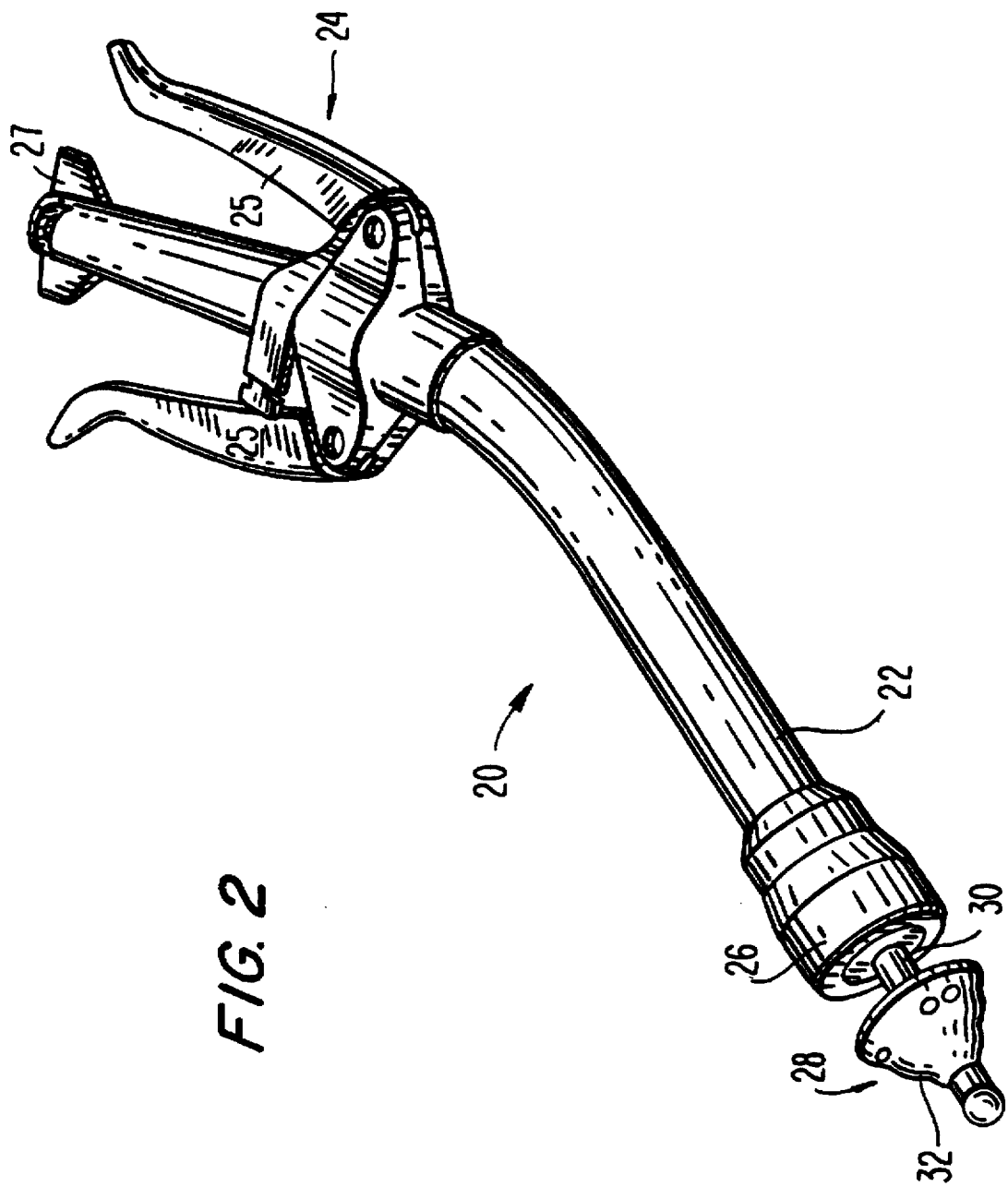
FIG. 2 is a perspective view of a surgical stapler apparatus for performing anastomosis of hollow tissue organs of the type contemplated by the present invention.

FIG. 1 illustrates a detachable anvil rod contemplated for use with devices for circular anastomosis. Referring now to FIG. 2, there is illustrated an apparatus 20 for stapling hollow tubular body organs as by circular anastomosis of intestines, colons or the like. Apparatus 20 may be any suitable surgical stapling instrument, for example, the PREMIUM CEEA™ surgical stapler, mentioned above. The apparatus may be utilized to attach two tubular body parts or one tubular body part to a non-tubular body part by circular anastomosis and may be adapted to attach the body parts by deformable metallic staples or bioabsorbable two-part body tissue fasteners.

Generally, apparatus 20 includes elongated shaft 22 and handle mechanism 24 attached to a proximal end of the elongated shaft. Handle mechanism 24 includes actuating handles 25 and adjusting wing nut 27. Fastener retainer component 26 is connected to the distal end of shaft 22 and houses an annular array of staples therein. A staple firing mechanism expels the staples from fastener retainer component 26.

An anvil component 28 is detachably mounted to the distal end of elongated shaft 22 by a mounting mechanism within the shaft which cooperatively engages the anvil component. Anvil component 28 includes detachable anvil rod 30 with attached anvil head 32. Anvil head 32 includes staple receiving buckets (not shown) to receive the staples expelled by the staple firing mechanism to clinch the staples and effect joining of the adjacent tissue sections.

Figure 3:
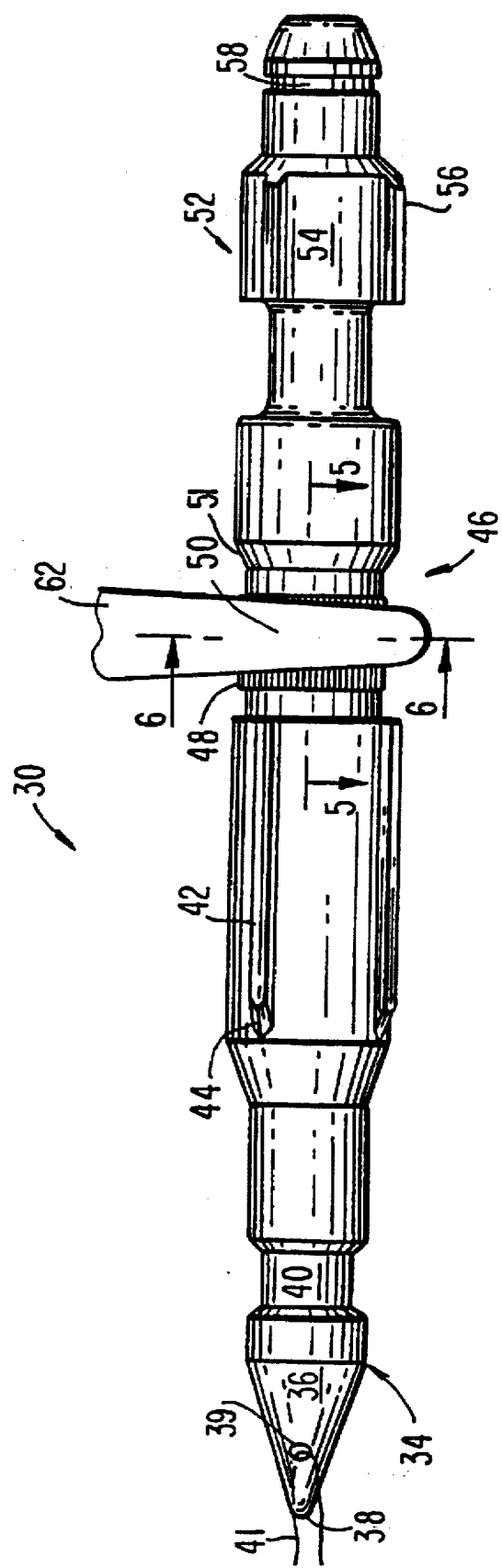
FIG. 3 is a side plan view of the detachable anvil rod constructed according to the present invention illustrating the use of a grasping tool to grasp the rod.

Referring now to FIG. 3, there is illustrated the detachable anvil rod 30 constructed according to the present invention. Anvil rod 30 is intended to be used with apparatus 20 and includes proximal section 34 which is received within and engages the mounting mechanism within the distal end of apparatus 20. Proximal section 34 includes a generally conical shaped mounting portion 36 which defines a diameter which gradually increases from mounting tip 38 towards the remainder of the rod. This gradual increase provides a relatively narrow mounting portion as compared to the mounting portion of the rod shown in FIG. 1. Such narrow configuration of mounting portion 36 facilitates mounting of rod 30 to the apparatus in the limited space provided in the operative site, and it increases the range of angular positions at which the rod may be oriented during introduction into the body and during introduction and withdrawal from the distal end of the apparatus. This advantage is provided by the fact that the diameter of the entry portion of rod 30 is significantly less than the diameter of elongated shaft 22 of apparatus 20, thus enabling the mounting portion to be readily received within the shaft.

Mounting tip 38 is rounded as shown to prevent undesired piercing of mounting portion 36 through tissue. An aperture 39 extends through portion 36 and is adapted to receive a flexible elongated member 41. Elongated member 41 may be a suture thread or the like and is provided to facilitate maneuvering rod 30 about the operative site. In particular, the surgeon may grasp member 41 with a grasping instrument or the like and pull the rod 30 about the operative site or through organ tissue without directly engaging the rod with the instrument.

Proximal section 34 of anvil rod 30 also includes an annular recess 40. Recess 40 is correspondingly configured to be engaged by the mounting mechanism within the distal end of elongated shaft 22 of the apparatus. A plurality of longitudinally extending external splines 42 are disposed in the general midportion of anvil rod 30. Splines 42 engage correspondingly configured and positioned longitudinal internal splines in the distal end of elongated shaft 22 during mounting of the rod to the apparatus to ensure proper alignment of the rod with the staple firing mechanism. Each external spline 42 has a chamfered and sloped proximal end 44. Chamfered ends 44 engage the internal splines within elongated shaft 22 and cause the rod to rotate slightly if the internal and external splines are initially misaligned during mounting so as to ensure proper mating between the two components.

Referring further to FIG. 3, anvil rod 30 includes grasping portion 46 adjacent external splines 42. Grasping portion 46 is advantageously reduced in cross-section and includes an irregular surface 48 having a plurality of longitudinal grooves which define a plurality of raised engaging ridges 50. Ridges 50 of irregular surface 48 are particularly adapted to engage the jaw members 62 of a grasping device as shown so as to facilitate gripping engagement therebetween.

Distal section 52 of anvil rod 30 includes an anvil head mounting collar 54 for mounting anvil head 32 (FIG. 2) to the rod. Collar 54 includes a plurality of longitudinally extending external splines 56 which engage with cooperating longitudinally extending internal splines in the anvil head to properly align the staple-receiving buckets in the anvil head with the staples in fastener retainer component 26. A circumferential groove 58 is formed adjacent collar 54 and is adapted to receive a U-shaped clamp which securely retains the anvil head on the collar.

Referring now to FIG. 4A, an endoscopic grasping device 60 suitable for grasping and maneuvering anvil rod 30 when used in endoscopic or laparoscopic procedures is illustrated. This grasping device is disclosed in U.S. patent application Ser. No. 07/593,670, filed Oct. 5, 1990, the contents of which are incorporated by reference, and includes a pair of reciprocating jaw members 62 which pivot in response to the opening and closing of handle member 63. As shown in FIG. 4B, the jaw members 62 of this device have gripping surfaces defined by a plurality of generally transverse serrations 64. Serrations 64 are cooperatively engaged by raised ridges 50 of the anvil rod. Another endoscopic grasping device similarly suitable for grasping anvil rod 30 is disclosed in U.S. patent application Ser. No. 07/834,687, filed Feb. 12, 1992, the contents of which are incorporated by reference. This grasping device features an endoscopic portion having an articulating section which is pivotable within about a 90° section of rotation. Jaw members are connected to the articulating section.

Referring now to FIGS. 5 and 6, when jaw members 62 of grasping device 60 are applied to the irregular surface 48 of grasping portion 46, ridges 50 cooperatively engage serrations 64 on the jaw members so as to form a gripping interlocking engagement between the two components. Such gripping engagement enables the surgeon to maneuver anvil rod 30 about the surgical site where blood and other bodily fluids are present with minimal risk of slippage of the rod from the grasping device, particularly during mounting of the rod to the instrument. It is to be appreciated that jaw members 62 of the grasping device can be applied to the rod at various angles while still maintaining a gripping engagement between the two components.

Referring again to FIG. 3, taken in conjunction with FIG. 5, a tapered surface 51 extends from grasping portion 46 forming a frusto-conical surface as shown. Frusto-conical surface 51 accommodates a portion of jaws 62 that may extend beyond grasping portion 46 and onto the tapered surface when the jaws are angularly applied to the grasping portion, thus enabling the jaws to close and sustain the gripping relationship between anvil rod 30 and the grasping tool. The angled surface also facilitates access to grasping portion 46. A second tapered frusto-conical surface 51 may also be provided as shown in FIG. 7, to provide increased flexibility for the surgeon by enabling the surgeon to apply the grasping tool to the rod at varying angular orientations. In an alternative embodiment, intermediate section does not include any tapered surfaces, as shown in FIG. 8.

Although the grasping portion of anvil rod has been described in terms of being engagable with the jaws of a grasping device of the type illustrated in FIG. 4A, it is to be appreciated that the irregular surface of grasping portion 46 may interlockingly engage a variety of other grasping instrumentation having varying jaw structure configurations.

Figure 9:
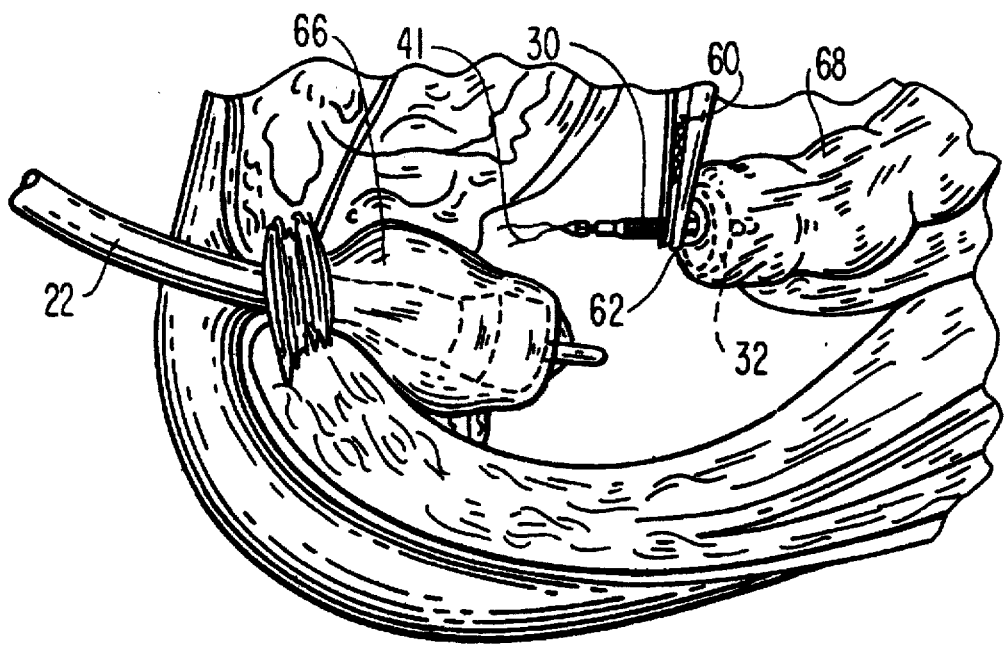
FIG. 9 is a perspective view of the intestinal area of a patient illustrating the procedure for positioning the surgical apparatus and the anvil rod of the present invention within intestinal sections prior to mounting the anvil rod to the apparatus.
Figure 10:
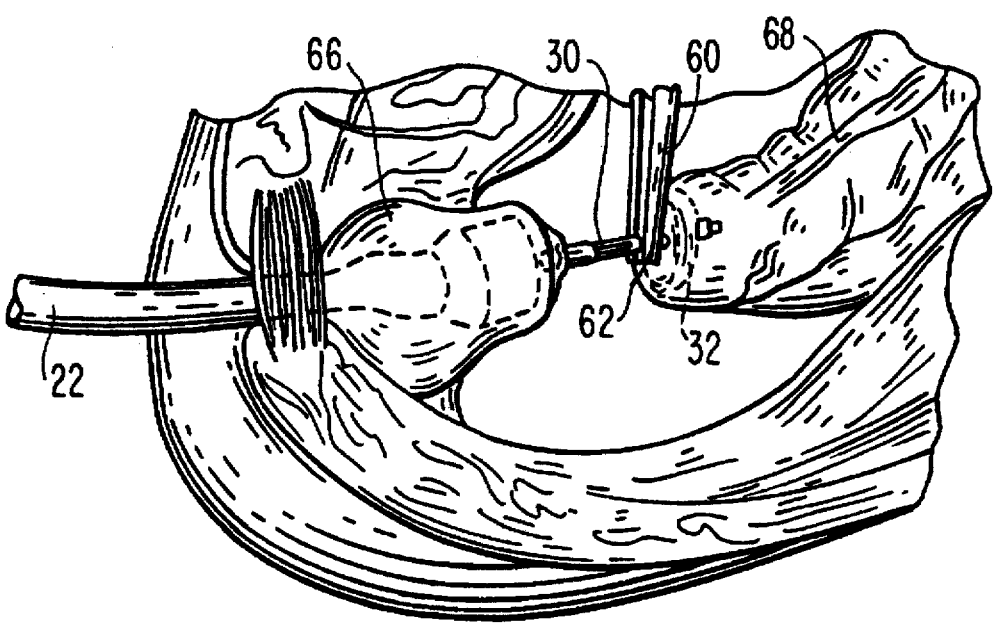
FIG. 10 is a perspective view similar to the view of FIG. 10 illustrating mounting of the anvil rod of the present invention to the distal end of the surgical apparatus.

FIGS. 9 and 10 illustrate the use of apparatus 20 and detachable anvil rod 30 in an anastomosis procedure to effect joining of intestinal sections 66, 68. Preferably, the anastomosis procedure is performed using minimally invasive surgical techniques including laparoscopic means and instrumentation. At the point in the procedure shown in FIG. 9, a diseased intestinal section had been previously removed preferably with a laparoscopic instrument applied to the operative site through an appropriate trocar sleeve. Anvil rod 30 with the attached anvil head 32 had been applied to the surgical site preferably either through a surgical incision or transanally and positioned within intestinal section 68. Elongated shaft 22 of apparatus 20 had been inserted transanally into intestinal section 66 Both intestinal sections 66, 68 are also shown temporarily secured about their respective components by conventional means such as a purse string stitch.

In completing the anastomosis, the surgeon through an appropriate trocar sleeve probes within the intestinal section to grasp anvil rod 30. Initially, the surgeon may grasp elongated member 41 to maneuver or pull rod 30 from intestinal section 68 so as to expose grasping portion 46. Thereafter, the surgeon engages irregular surface 48 of grasping portion 46 with jaw members 62 of tool 60, and maneuvers rod 30 towards the distal end of elongated member 22. Mounting portion 36 of rod 30 is then inserted within the distal end of elongated shaft 22 of the apparatus, as shown in FIG. 10, wherein the mounting mechanism within the distal end of the shaft engages the rod to effect the mounting. Thereafter, the anvil component and elongated shaft are approximated, and the apparatus is fired to complete the anastomosis.

Figure 11:
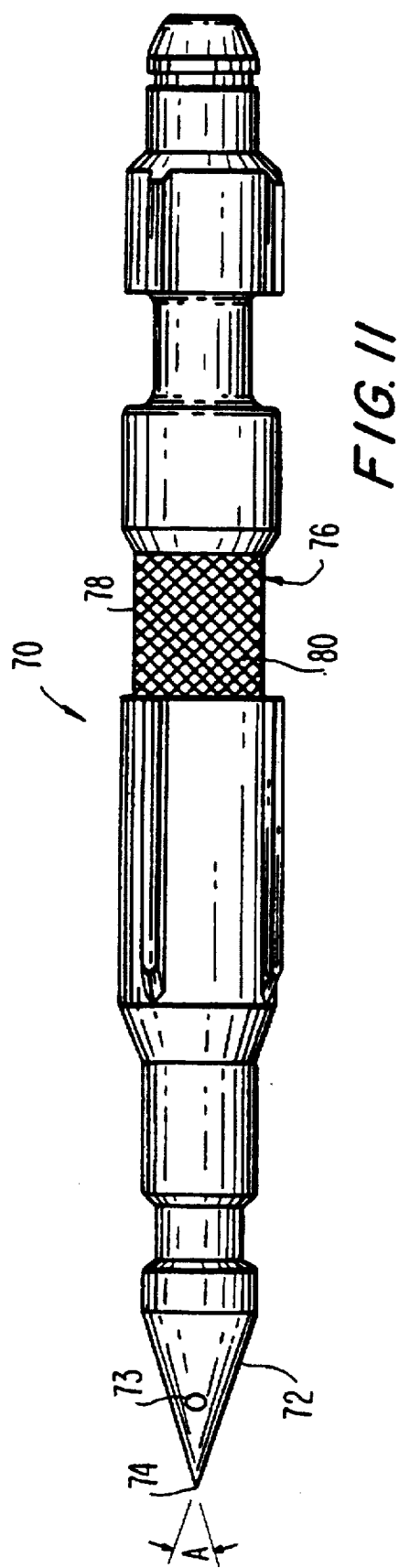
FIG. 11 is a side view of a further alternative embodiment of the anvil rod of the present invention.
Figure 12:
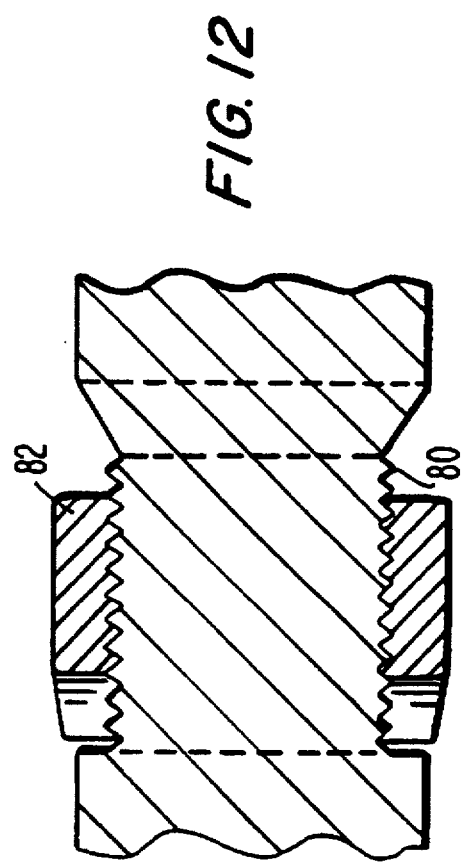
FIG. 12 is a side view of another alternative embodiment of the anvil rod of the present invention.

Referring now to FIGS. 11–12, an alternative embodiment of the anvil rod of the present invention is illustrated. Rod 70 is similar to the rod described in the embodiment of FIG. 3 except that mounting portion 72 of this rod defines a pointed or piercing mounting tip 74. Piercing mounting tip is relatively sharp to enhance piercing and penetration of rod 70 through tissue. Such piercing quality is desirable in certain procedures. Preferably, piercing tip 74 defines an angle A ranging in value from about 5° to about 40°. A mounting tip within this angular range will define a relatively narrow mounting portion to enhance mounting of the rod to instrument 20. In a preferred embodiment, angle A is about 20°. Rod 70 also includes a grasping portion 76 having an irregular surface 78 of reduced cross section and defined by a plurality of intersecting grooves and ridges 80, preferably formed by knurling. Ridges 80 of irregular surface 78 are particularly adapted to engage the jaw members 82 of a grasping device as shown in FIG. 12 to form an interlocking arrangement between the two components.

Figure 13:
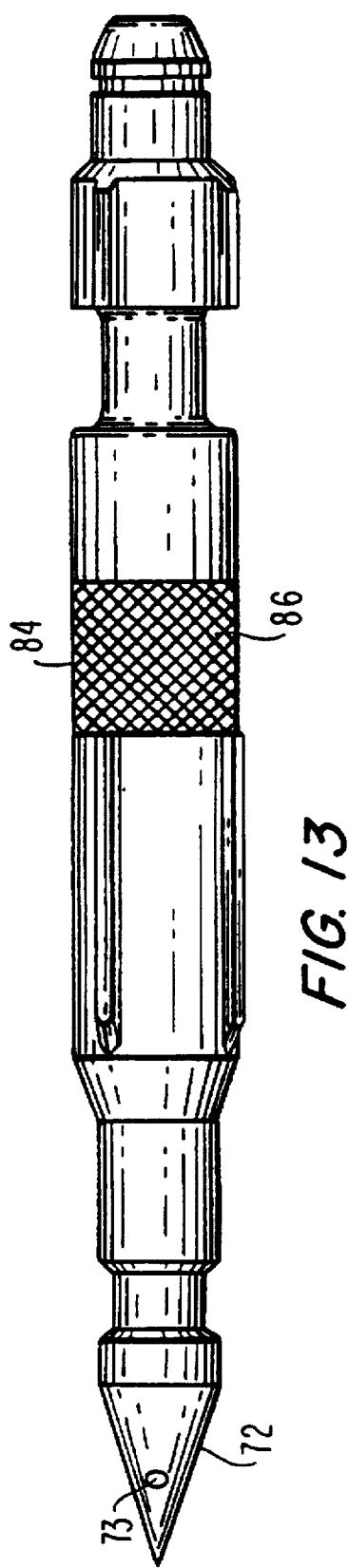
FIG. 13 is a side view of yet another alternative embodiment of the anvil rod of the present invention.

FIG. 13 illustrates another preferred embodiment of the anvil rod wherein grasping portion 84 has a cross-sectional diameter which is substantially equal to the diameter of adjacent rod portions. Ridges 86 are defined by a plurality of intersecting grooves.

Figure 14:
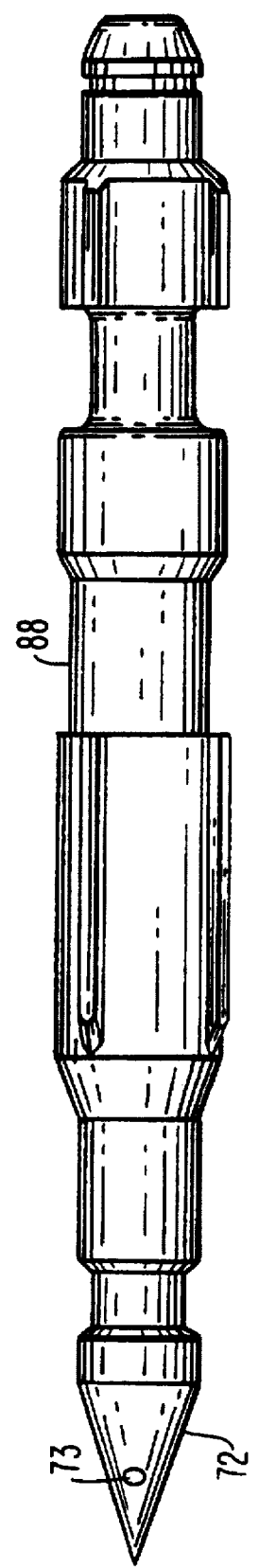
FIG. 14 is a side view of still another alternative embodiment of the anvil rod of the present invention.

Referring now to FIG. 14, another embodiment of the anvil rod of the present invention is illustrated. In the embodiment, grasping portion 88 has a reduced cross section with a finished surface and no intersecting grooves and ridges. The advantages of the reduced cross section are as described hereinabove.

The embodiments described in FIGS. 11-14 each include a mounting portion 72 which may be provided with an aperture 73 for reception of an elongated member. The advantages of the aperture 73 and the elongated member are as described hereinabove.

It will be understood that various modifications can be made to the embodiments of the present invention herein described without departing from the spirit thereof. The invention in its broader aspects therefore is not limited to the specific embodiments herein shown and described but departures may be made therefrom within the scope of the accompanying claims without departing from the principals of the invention and without sacrificing its chief advantages.

What is claimed is:

1. A detachable anvil assembly which comprises an elongated anvil rod including a proximal end portion, a distal end portion and an irregular surface portion intermediate the proximal and distal end portions, the irregular surface portion including a recessed portion, the recessed portion defining a reduced cross-section relative to portions of the anvil rod adjacent the recessed portion, the recessed portion including a plurality of grooves wherein adjacent grooves define ridges therebetween, and an anvil head mounted to the distal end portion of the anvil rod, the anvil head defining a generally annular staple forming surface.

2. The detachable anvil assembly according to claim 1, wherein the recessed portion defines a generally circular cross section.

3. The detachable anvil assembly according to claim 2, wherein the grooves and ridges are disposed about the circumference of the recessed portion.

4. The detachable anvil assembly according to claim 1, wherein the grooves of the recessed portion intersect and are oriented at generally opposite angles with respect to each other.

5. The detachable anvil assembly according to claim 1, wherein the anvil rod includes at least one frusto-conical surface adjacent the recessed portion.

6. The detachable anvil assembly according to claim 5, including two opposed frusto-conical surfaces adjacent the recessed portion.

7. The detachable anvil assembly according to claim 1, wherein the proximal end portion of the anvil rod defines a generally tapered mounting portion for mounting to an apparatus for ejecting a circular array of surgical staples.

8. The detachable anvil assembly according to claim 7, wherein the mounting portion is generally frusto-conically shaped.

9. The detachable anvil assembly according to claim 1, wherein the anvil rod includes a second recessed portion, the second recessed portion being disposed between the first mentioned recessed portion having the grooves and ridges and the distal end portion of the anvil rod, the second recessed portion for accommodating a purse string stitch and defining a reduced cross section relative to portions of the anvil rod adjacent the second recessed portion.

10. The detachable anvil assembly according to claim 9, wherein the second recessed portion defines a generally circular cross section.

11. In combination, an apparatus for performing circular anastomosis and an anvil rod detachably mounted to the apparatus, the anvil rod comprising an elongated rod member having a proximal end portion for mounting the rod member to the apparatus, a distal end portion for supporting an anvil head and an intermediate portion disposed between the proximal and distal end portions, the intermediate portion including a grasping portion to be engaged by grasping surfaces of a grasping instrument so as to enhance gripping engagement therebetween, the grasping portion including a first recessed portion defining a reduced cross-section relative to portions of the rod member adjacent the first recessed portion, the first recessed portion having a plurality of grooves wherein adjacent grooves define ridges therebetween, and a second recessed portion disposed between the grasping portion and the distal end portion for accommodating a purse string stitch, the second recessed portion defining a reduced-cross section relative to portions of the rod member adjacent the recessed portion.

12. A detachable anvil rod for use with an apparatus for performing circular anastomosis, which comprises an elongated shaft member having a proximal end portion defining a tapered mounting portion for mounting to the apparatus, a distal end portion for supporting an anvil head and an intermediate portion disposed between the proximal and distal end portions, the intermediate portion including a recessed portion having a reduced cross section relative to portions of the shaft member adjacent the recessed portion, the recessed portion including a plurality of ridges, the ridges engageable with grasping surfaces of a grasping instrument so as to facilitate gripping engagement therebetween.

13. The detachable anvil rod according to claim 12, wherein the mounting portion is conically shaped.

14. A detachable anvil assembly, which comprises an elongated anvil rod including a proximal end portion having a generally tapered mounting portion to facilitate mounting to an apparatus for performing circular anastomosis, a distal end portion and an irregular surface portion disposed intermediate the proximal and distal end portions, the irregular surface portion defining a roughened surface portion having a plurality of ridges for facilitating engagement with grasping surfaces of a grasping instrument, and an anvil head mounted to the distal end portion of the anvil rod, the irregular surface portion defining a cross-sectional dimension less than a cross-sectional dimension of portions of the anvil rod proximate the irregular surface portion, the proximal end portion of the anvil rod further including at least one spline disposed adjacent the irregular surface portion, the one spline of the anvil rod engageable with a cooperating spline at the distal end of the apparatus to assist in mounting the anvil rod to the apparatus.

15. The detachable anvil assembly according to claim 14 wherein the at least one spline of the anvil rod is an external spline.

16. The detachable anvil assembly according to claim 15 wherein the distal end portion of the anvil rod includes at least one spline for engaging with a corresponding spline disposed within the anvil head to assist in mounting the anvil head to the anvil rod.

17. The detachable anvil assembly according to claim 16 wherein the one spline of the distal end portion of the anvil rod is an external spline and wherein the corresponding spline of the anvil head is an internal spline.

18. A detachable anvil assembly which comprises an elongated rod including a proximal end portion having a generally tapered mounting portion for facilitating mounting to an apparatus for performing circular anastomosis, a distal end portion and an irregular surface portion intermediate the proximal and distal end portions, and an anvil head supported by the distal end portion, the irregular surface portion defining a roughened surface having a plurality of intersecting grooves defined therein, the roughened surface to be engaged by grasping surfaces of a grasping instrument to enhance gripping engagement therebetween.

19. In combination, an apparatus for performing circular anastomosis and an anvil rod, the anvil rod including an elongated rod member having a proximal end portion, a distal end portion with an anvil head mounted thereto and an intermediate portion disposed between the proximal and distal end portions, the proximal end portion of the anvil rod including a generally tapered mounting portion for facilitating mounting to the apparatus and having at least one spline to cooperate with a corresponding spline at the distal end of the apparatus to detachably mount the anvil rod, the intermediate portion of the anvil rod including a grasping portion, the grasping portion reduced in cross-section relative to portions of the anvil rod proximate the grasping portion and defining a roughened surface to be engaged by grasping surfaces of a grasping instrument so as to enhance gripping engagement therebetween.

* * * * *